United States Patent [19]

Sharpe et al.

[11] Patent Number: 5,499,997
[45] Date of Patent: Mar. 19, 1996

[54] ENDOSCOPIC TENACULUM SURGICAL INSTRUMENT

[75] Inventors: Leslie A. Sharpe, Edina, Minn.; Francis C. Peterson, Prescott, Wis.

[73] Assignee: Sharpe Endosurgical Corporation, St. Paul, Minn.

[21] Appl. No.: 186,484

[22] Filed: Jan. 18, 1994

Related U.S. Application Data

[63] Continuation of Ser. No. 867,173, Apr. 10, 1992, abandoned.

[51] Int. Cl.$^6$ ...................................................... A61B 17/28
[52] U.S. Cl. ................................................. 606/206; 606/205
[58] Field of Search ................................. 606/205–207

[56] References Cited

U.S. PATENT DOCUMENTS

| | | |
|---|---|---|
| 86,016 | 1/1869 | Howell . |
| 463,785 | 11/1891 | Connable et al. . |
| 987,173 | 3/1911 | Sale . |
| 2,137,710 | 11/1938 | Anderson ........................... 606/206 |
| 3,404,677 | 7/1965 | Springer . |
| 3,404,683 | 10/1968 | Eizenberg ........................... 606/207 |
| 3,844,291 | 10/1974 | Moen . |
| 3,989,049 | 11/1976 | Yoon . |
| 4,174,715 | 11/1979 | Hasson . |
| 4,226,239 | 10/1980 | Polk et al. . |
| 4,248,233 | 2/1981 | Zeppelin et al. .................... 606/207 |
| 4,374,523 | 2/1983 | Yoon . |
| 4,467,802 | 8/1984 | Maslanka ........................... 128/321 |
| 4,493,319 | 1/1985 | Polk et al. ......................... 128/303 A |
| 4,724,838 | 2/1988 | Hasson ............................... 606/207 |
| 4,917,100 | 4/1990 | Nottke . |
| 4,994,079 | 2/1991 | Genese et al. . |

FOREIGN PATENT DOCUMENTS

| | | | |
|---|---|---|---|
| 2346401 | 3/1974 | Germany ........................... 606/206 |

OTHER PUBLICATIONS

WISAP Semm System, Minimal Invasive Surgery, Biopsy Instruments 5 mm.

*Primary Examiner*—Randall L. Green
*Assistant Examiner*—Mark O. Polutta
*Attorney, Agent, or Firm*—Merchant, Gould, Smith, Edell, Welter & Schmidt

[57] ABSTRACT

The present invention is directed to an endoscopic grasping tool for use inside a patient. As the teeth of the tenaculum come together they are positioned by a complimentary pair of contact pads. In this retracted position the distal end of the instrument does not present any sharp edges.

5 Claims, 3 Drawing Sheets

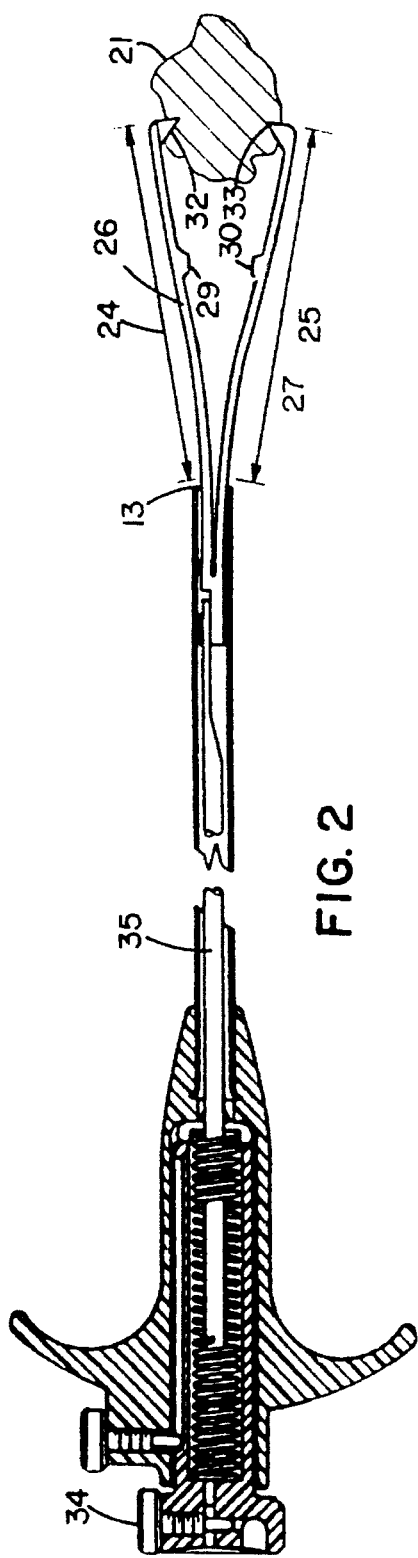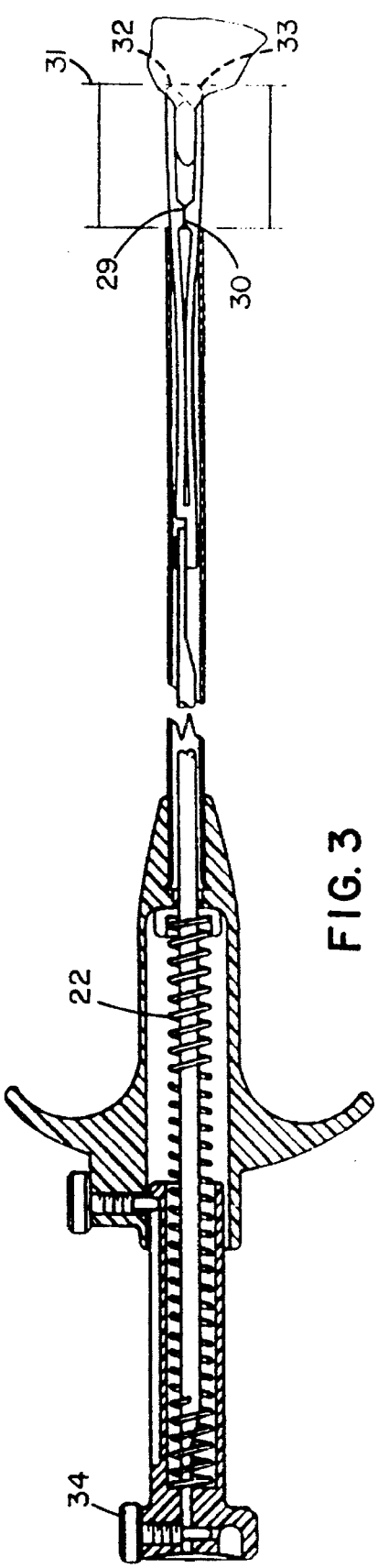

5,499,997

ENDOSCOPIC TENACULUM SURGICAL INSTRUMENT

This is a continuation of application Ser. No. 07/876,173, filed Apr. 10, 1992, now abandoned.

BACKGROUND OF THE INVENTION

1. Technical Field

The present invention relates to surgical instruments for use during laparoscopic surgery. More particularly, the invention is directed to a grasping tool for use inside the abdominal cavity.

2. Description of the Prior Art

The typical laparoscopic surgical procedure begins with the puncture of the patient's abdominal wall and the placement of an access port. Next, gas is admitted to the abdominal cavity partially inflating it, forming a pneumoperitoneum. Next a laparoscope or endoscope is inserted through the access port to permit viewing of the organs during the surgical procedure. Typically, the laparoscope has both an eyepiece for direct use by the physician and a video monitor to permit visualization of the surgical field. Additional access ports may be located elsewhere on the patient's abdominal wall to permit insertion of surgical instruments. Access ports come in a variety of diameters and 5, 7 and 11 millimeter ports are widely used for surgery within the peritoneal cavity. Instruments for insertion through such ports are readily available to practitioners and numerous surgical grasping instruments are available to surgeons specializing in these procedures. See for example:

U.S. Pat. No. 2,034,785 which teaches the use of a hinged jaw set which closes with a remote handle structure.

U.S. Pat. No. 3,404,677 also teaches the use of a jaw set. In this reference a spring is used to bias the jaw set into an open position. When the jaw set is retracted into the tube, the teeth close.

U.S. Pat. No. 4,226,239 teaches a jaw set having a single tooth on each jaw. This jaw set concentrates the closing force imparted by the jaws onto a point.

SUMMARY OF THE INVENTION

The present invention is directed to an endoscopic grasping tool. The tool includes an operating handle coupled to an elongate sheath. The grasping structure extends beyond the distal tip of sheath and includes a pair of complimentary jaw arms. The jaw arms support a pair of distal sharp-pointed teeth located on opposing jaw arms for piercing and holding large tissue masses. The control handle can retract the jaw arms placing the teeth in the meshed position where no sharp surfaces are presented to tissue. Similarly the control handle can advance the jaw arms and open the jaw set presenting the sharp teeth of the jaw set. Motion of the jaw arms towards the retracted position brings complementary contact pads into contact. When the contact pads touch the sharp-pointed teeth are supported in a cantilever fashion anchored at the contact pad point. In this position the teeth mesh and present a blunt surface which enhances the safety of the tool. In this position the bending moment is defined by the distance between the pads and the teeth. When grasping large structures which prevent the contact pads from touching the bending moment is defined by the length of the arm extending beyond the distal tip to the teeth.

BRIEF DESCRIPTION OF THE DRAWING

Throughout the several figures of the drawing like reference numerals are used to identify identical structure, wherein:

FIG. 2 is a cross-section of the instrument depicting the control handle and the tenaculum jaw set in the extended and open position;

FIG. 3 is a cross-section of the instrument depicting the control handle and the tenaculum jaw set in the retracted and closed position;

DETAILED DESCRIPTION OF THE ILLUSTRATIVE EMBODIMENT

Figure 1:
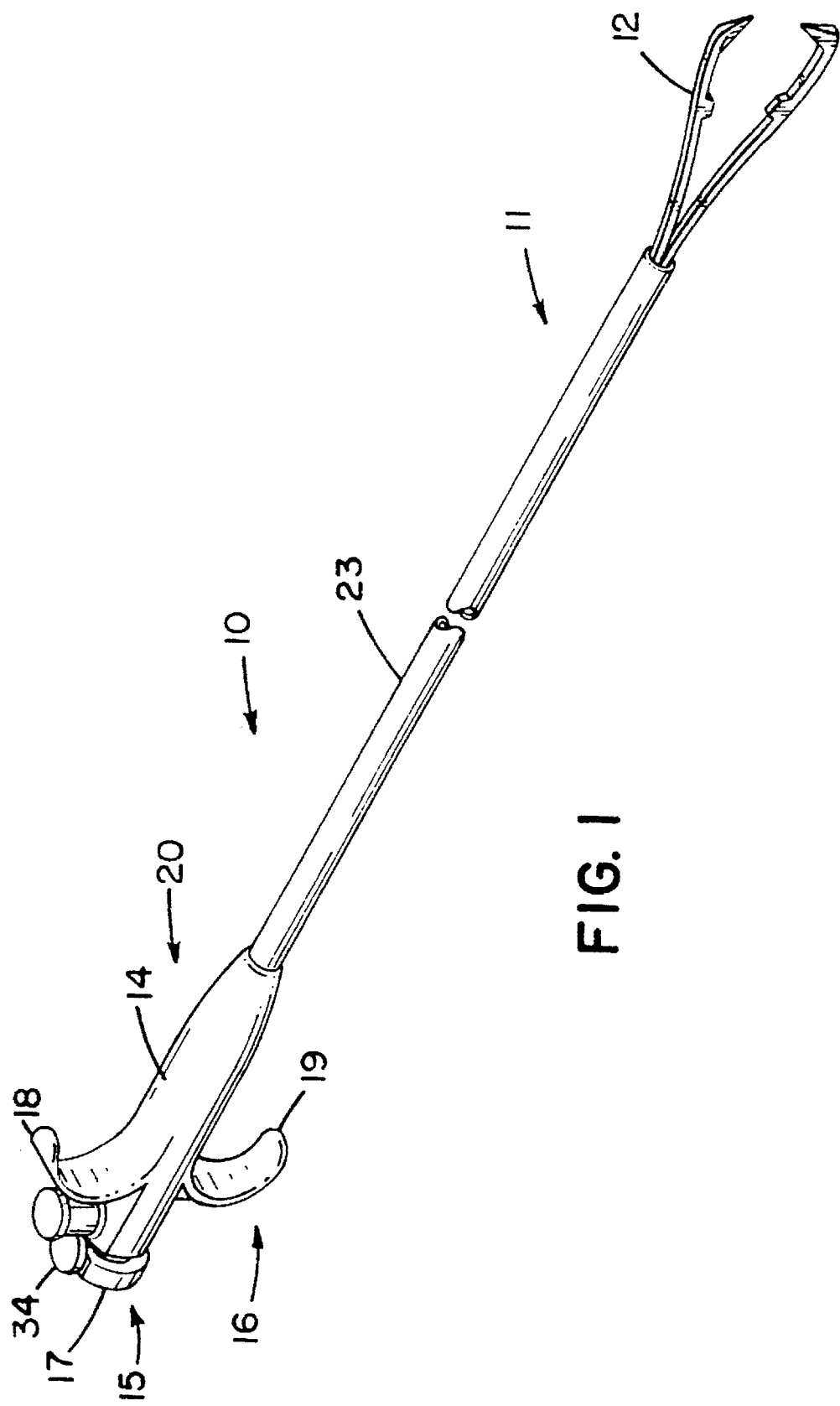
FIG. 1 is a perspective view of the assembled endoscopic tenaculum surgical instrument.

FIG. 1 is a perspective view of the endoscopic tenaculum surgical instrument 10. The anterior section 11 of the instrument 10 houses tenaculum jaw set 12. The posterior section 20 of the instrument 10 includes the control handle structures generally designated 14. The control handle 14 is grasped by the surgeon and the anterior section 11 is inserted into the body cavity through a suitable port. In use, the surgeon operates the control handle 14 to manipulate the tenaculum jaw set 12. The instrument 10 is well suited to blunt dissection of tissues with the jaw set closed. The instrument 10 is also well suited to grasping tissue pedicles and other structures with the jaw set opened.

The control handle 14 includes a rear grip structure 15 and a foregrip structure 16. In use the rear grip 15 and foregrip 16 are squeezed together to operate the instrument. The squeezing motion compresses a spring 22 which biases the jaw set into the closed position. The preferred rear grip is a pommel 17, while the preferred foregrip 16 comprises a pair of complimentary loops 18 and 19. These grip structures together form a symmetrical control handle 14. This symmetrical grip arrangement makes the instrument 10 operable with either the left or right hand. The symmetry also permits the instrument 10 to be operated in an upright position or an inverted position when rotated through 180 degrees. The assembly screw 34 provides the surgeon with a tactile and visual reference for the orientation of the tenaculum jaw set 12. The preferred semi-circular loops 18 and 19 may receive the forefinger and middle finger of the surgeon while the surgeon's thumb rests on the pommel 17. This preferred control handle 14 also can readily accept the surgeon's middle and ring finger on the loops 18 and 19 and palm on the pommel 17. This ambidextrous multi-position control handle 14 is also compact and light weight which materially aids the surgeon's control of the operating portion of the instrument. These preferred grip structures are preferably molded of medical grade polysulfone plastic molded onto a stainless steel tubular sheath 23.

In FIG. 2 the instrument 10 is shown in cross-section with the tenaculum jaw set 12 in the open position. The cross-section view shows the assembly screw 34 in the rear grip 15 which connects to one end of the connector rod 35. With the screw 34 removed the connector rod 35 and attached tenaculum jaw set 12 can be removed, from the tubular sheath 23 by movement toward the posterior section 20 of the instrument. With the connector rod 35 removed, the tenaculum jaw set 12 can be detached from the connector rod 35. In general the tenaculum jaw set 12 will form a disposable assembly which is discarded or cleaned after a single surgical use. Although any one of a number of connectors can be used to couple the tenaculum jaw set 12 to the connector rod 35, the preferred connector is a plug in slot structure shown in FIG. 2 and FIG. 3. In embodiments where the entire tool is disposable, the assembly screw 34 may be replaced with a pin preventing unauthorized disassembly.

The foregrip assembly 16 also contains a rubber gas seal 38 which encircles the circular connector rod 35. This gas seal 38 prevents passage of fluid or gas through the instrument 10 and therefore maintains pneumoperitoneum, and sterility of the surgical field.

In FIG. 2 the surgeon has squeezed the control handle 14 and compressed the spring 22 to extend the tenaculum jaw set 12 to the open position and then released the pommel 17 to grasp the fibrous tissue mass 21. In this position the force between the first jaw arm 26 and the second jaw arm 27 is defined by the first moment arm 24 and the second moment arm 25. These moments are generated by the length of the first jaw arm 26 as it extends beyond the distal tip 13 of the sheath 23 and the length of the second jaw arm 27 as it extends from the distal tip 13 of sheath 23. The spring 22 has a first end 42 which abuts the handle near the pommel, and a second end 43 which helps to retain the gas seal 38 into position in the fore grip. The drawing shows that the spring is concentric with the connector rod.

In FIG. 3 the surgeon has relaxed his grip on the control handle 14 to retract the tenaculum jaw set 12 to the closed position around a gauze sponge 28 or the like. In this retracted position the grasping force between the first jaw arm 26 and the second jaw arm 27 is defined by the location of the first contact pad 29 and the second contact pad 30 and the distal end 31 of the jaw arms. In this position the abutment between the first contact pad 29 and the second contact pad 30 prevents the first tooth 32 from scissoring past the second tooth 33.

Figure 4:
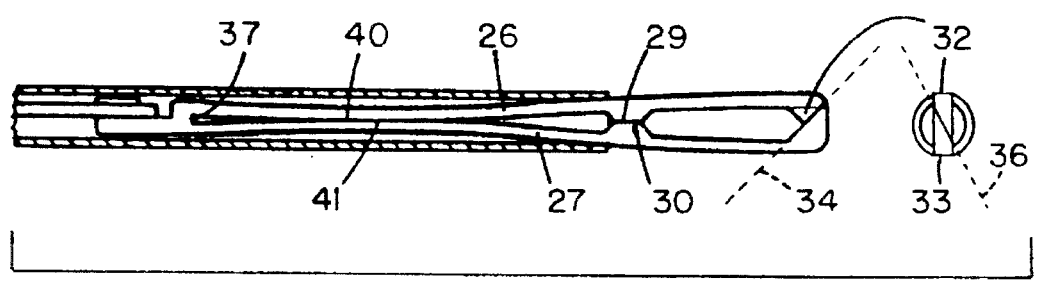
FIG. 4 is a view of the tenaculum jaw set in the retracted and closed position; and, FIG. 5 is a view of the tenaculum jaw set in the extended and open position.

FIG. 4 is a view of the tenaculum jaw set in the retracted and closed position. In this position the first tooth 32 and the second tooth 33 mesh along a line of contact 36. The contact between the first contact pad 29 and the second contact pad 30 prevents any lateral displacement of the teeth which would otherwise expose a sharp edge. Consequently the distal end 31 of the instrument 10 can be safely used for blunt dissection without fear of tissue injury from a sharp edge.

Figure 5:
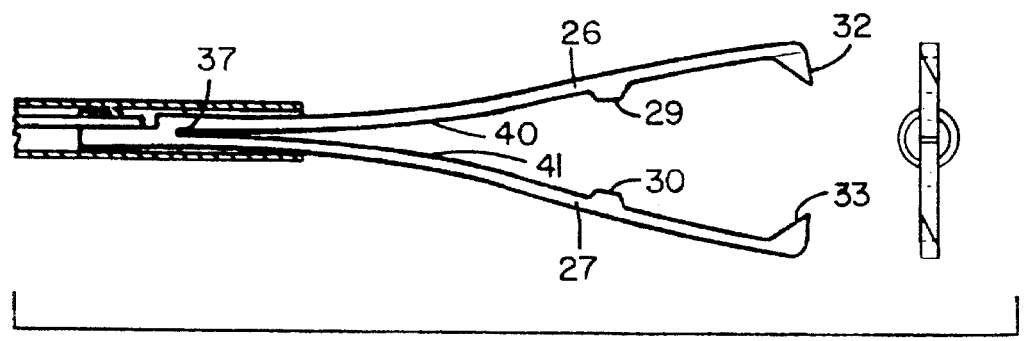

FIG. 5 shows the tenaculum jaw set 12 in the fully open position where the first tooth 32 and the second tooth 33 are exposed and can be used to snag or manipulate tissue masses or the like.

FIG. 4 and FIG. 5 taken together show another feature of the instrument 10. The first jaw arm 26 and the second jaw arm 27 are bifurcated at a notch point 37. The inner surface of the first arm 26 has an arcuate shape seen best in FIG. 4 The inner surface of the first arm has an apex surface 40. The second jaw arm 27 also has an apex surface 41 on its inner surface. As the arms are moved into the retracted position seen in FIG. 4 these two apex surfaces come together and contact each other. This contact effectively shortens the arms resulting in increased holding power in the retracted position. As best seen in the end views of FIG. 4 and FIG. 5 the arms have a substantially square form cross-section which increases the contact area between the first apex surface 40 and the second apex surface 41.

Although the illustrative tenaculum jaw set 12 depicted herein are formed from a unitary piece of metal or other material it should be appreciated that the jaw arms could be hinged together near their notch point 37 with the connector rod 35. Similarly, the preferred jaw arms are of substantially uniform cross-section along there entire length, however it should be appreciated that the this cross-section may be varied along the length of the arms as well. In a similar fashion the tubular sheath is shown with a circular cross-section to facilitate sealing with the port, however non circular cross-sections are operable as well. Although the two tooth jaw set depicted herein is believed to be the most useful configurations for general surgery, the number of teeth may be increased in accordance with the teaching of this disclosure without departing from the scope of the invention.

What is claimed is:

1. An endoscopic grasping tool surgical instrument for grasping tissue and the like comprising:

a control handle, having a foregrip and having a rear grip;

a tubular sheath coupled to said control handle;

a connector rod coupled to said control handle, and adapted for reciprocating motion within said tubular sheath;

a first jaw arm, having a first tooth for engaging said tissue;

a second jaw arm, having a second tooth for engaging said tissue;

said first jaw arm and said second jaw arm being coupled to said connector rod, and adapted to be moved to an extended position by motion of said connector rod, and adapted to be moved to a retracted position by motion of said connector rod;

said first jaw arm having a distal first contact pad;

said second jaw arm having a distal second contact pad;

motion toward said retracted position placing said distal first contact pad and said distal second contact pad into contact, said first tooth and said second tooth intermeshing along a line of contact forming a blunt distal end;

a spring located in said control handle to provide biasing force to said first jaw arm and to said second jaw arm to bias said first jaw arm and said second jaw arm into said retracted position; and said first jaw arm and said second jaw arm having a substantially arcuate shape defining a first apex surface on said first jaw arm and defining a second apex surface of said second jaw arm, said first apex surface and said second apex surface being biased and in abutment to each other during motion toward said retracted position; and a gas seal within said control handle marked concentrically abut said connector rod.

2. An endoscopic grasping tool surgical instrument for grasping tissue and the like comprising:

a control handle, having a foregrip and having a rear grip;

a tubular sheath coupled to said control handle, said sheath including an internal lumen;

a connector rod coupled to said control handle, and adapted for reciprocating motion within said tubular sheath;

a first jaw arm, having a first tooth for engaging said tissue;

a second jaw arm, having a second tooth for engaging said tissue;

said first jaw arm and said second jaw arm being coupled to said connector rod, and adapted to be moved to an extended position by motion of said connector rod, and adapted to be moved to a retracted position by motion of said connector rod, said first jaw arm and said second jaw arm being formed from a unitary piece of material bifurcated at a notch point to form said first jaw arm and said second jaw arm;

said first jaw arm having a distal first contact pad;

said second jaw arm having a distal second contact pad;

motion toward said retracted position placing said distal first contact pad and said distal second contact pad into contact, said first tooth and second tooth intermeshing along a line of contact forming a blunt distal end;

said first jaw arm and said second jaw arm having substantially square form cross sections along their length from a point proximate said notch point to a position proximate said first and second contact pads;

the width of said first and second contact pads in the direction normal to said pads exceeding the diameter of the lumen of said tubular sheath;

said spring retracting said first jaw arm and said second jaw arm to a relaxed position determined by contact between said first contact pad with said second contact pad;

a spring located in said control handle to provide biasing force to said first jaw arm and to said second jaw arm to bias said first jaw arm and said second jaw arm into said retracted position; and said first jaw arm and said second jaw arm having a substantially arcuate shape defining a first apex surface on said first jaw arm and defining a second apex surface of said second jaw arm, said first apex surface and said second apex surface being biased and in abutment to each other during motion toward said retracted position.

3. An endoscopic grasping tool surgical instrument for grasping tissue and the like, comprising:

a control handle, having a foregrip and having a rear grip;

a tubular sheath including an internal lumen, a proximal end and a distal end, said proximal end of said tubular sheath being coupled to said control handle;

a connector rod coupled to said control handle, and adapted for reciprocating motion within said tubular sheath;

a first jaw arm, having a first tooth for engaging said tissue;

a second jaw arm, having a second tooth for engaging said tissue, said first jaw arm and said second jaw arm being coupled to said connector rod, and adapted to be moved to an extended position by motion of said connector rod, and adapted to be moved to a retracted position by motion of said connector rod;

a distal first contact pad on said first jaw arm;

a distal second contact pad on said second jaw arm, said first jaw arm and said second jaw arm being aligned such that when said first jaw arm and said second jaw arm are moved toward said retracted position placing said distal first contact pad and said distal second contact pad into contact, said first tooth and said second tooth intermeshing along a line of contact forming a blunt distal end;

a spring located in said control handle to provide biasing force to said first jaw arm and to said second jaw arm to bias said first jaw arm and said second jaw arm into said retracted position;

said first jaw arm and said second jaw arm each having a substantially arcuate shape defining a first apex surface on said first jaw arm and defining a second apex surface on said second jaw arm, said first apex surface and said second apex surface being biased and in abutment to each other during motion toward said retracted position, generating a clamping force about said distal end of said tubular sheath while said first and second arms are in contact with said tubular sheath;

said first jaw arm and said second jaw arm having substantially square form cross-sections along their length from a point proximate said notch point to a position proximate said first and second distal contact pads;

said first jaw arm and said second jaw arm being formed from a unitary piece of material bifurcated at a notch point to form said first jaw arm and said second jaw arm;

the width of said first and second contact pads in the direction normal to said pads exceeding the diameter of said lumen of said tubular sheath; and said spring retracting said first jaw arm and said second jaw arm to a relaxed position determined by contact between said first contact pad with said second contact pad.

4. An endoscopic grasping tool surgical instrument for grasping tissue and the like, comprising:

a control handle, having a foregrip and having a rear grip;

a tubular sheath including an internal lumen, a proximal end and a distal end, said proximal end of said tubular sheath being coupled to said control handle;

a connector rod coupled to said control handle, and adapted for reciprocating motion within said tubular sheath;

a first jaw arm having a first tooth for engaging said tissue;

a second jaw arm having a second tooth for engaging said tissue, said first jaw arm and said second jaw arm being coupled to said connector rod, and adapted to be moved to an extended position by motion of said connector rod, and adapted to be moved to a retracted position by motion of said connector rod;

a distal first contact pad on said first jaw arm;

a distal second contact pad on said second jaw arm, said first jaw arm and said second jaw arm being aligned such that when said first jaw arm and said second jaw arm are moved toward said retracted position placing said distal first contact pad and said distal second contact pad into contact, said first tooth and said second tooth intermeshing along a line of contact forming a blunt distal end;

a spring located in said control handle to provide biasing force to said first jaw arm and to said second jaw arm to bias said first jaw arm and said second jaw arm into said retracted position, said spring having a helical shape and being positioned concentrically over said connector rod;

said first jaw arm and said second jaw arm each having a substantially arcuate shape defining a first apex surface on said first jaw arm and defining a second apex surface on said second jaw arm, said first apex surface and said second apex surface being biased and in abutment to each other during motion toward said retracted position, generating a clamping force about said distal end of said tubular sheath while said first and second arms are in contact with said tubular sheath;

said rear grip including a pommel;

said spring having a first end and a second end, wherein said first end abuts said rear grip proximate to said pommel and said second end abuts said foregrip proximate to said tubular sheath.

5. An endoscopic grasping tool surgical instrument for grasping tissue and the like, comprising:

a control handle, having a foregrip and having a rear grip;

a tubular sheath including an internal lumen, a proximal end and a distal end, said proximal end of said tubular sheath being coupled to said control handle;

a connector rod coupled to said control handle, and adapted for reciprocating motion within said tubular sheath;

a first jaw arm, having a first tooth for engaging said tissue;

a second jaw arm, having a second tooth for engaging said tissue, said first jaw arm and said second jaw arm being coupled to said connector rod, and adapted to be moved to an extended position by motion of said connector rod, and adapted to be moved to a retracted position by motion of said connector rod;

said first jaw arm having a distal first contact pad;

said second jaw arm having a distal second contact pad, said first jaw arm and said second jaw arm being aligned such that when said first jaw arm and said second jaw arm are moved toward said retracted position placing said distal first contact pad and said distal second contact pad into contact, said first tooth and said second tooth intermesh along a line of contact forming a blunt distal end;

a spring located in said control handle to provide biasing force to said first jaw arm and to said second jaw arm to bias said first jaw arm and said second jaw arm into said retracted position;

said first jaw arm and said second jaw arm each having a substantially arcuate shape defining a first apex surface on said first jaw arm and defining a second apex surface on said second jaw arm, said first apex surface and said second apex surface being biased and in abutment to each other during motion toward said retracted position, generating a clamping force about said distal end of said tubular sheath while said first and second arms are in contact with said tubular sheath; and a gas seal within said handle mounted concentrically about said connector rod.

* * * * *